United States Patent [19]

Haughton

[11] Patent Number: 5,060,530

[45] **Date of Patent: * Oct. 29, 1991**

[54] HOLDER FOR MOLTEN METAL SAMPLING DEVICE

[75] Inventor: Gary H. Haughton, Burlington, Canada

[73] Assignee: Evacuo Enterprises Limited, Ontario, Canada

[ * ] Notice: The portion of the term of this patent subsequent to Jul. 17, 2007 has been disclaimed.

[21] Appl. No.: 441,289

[22] Filed: Nov. 27, 1989

Related U.S. Application Data

[63] Continuation-in-part of Ser. No. 240,506, Sep. 6, 1988, Pat. No. 4,932,271, and a continuation-in-part of Ser. No. 406,529, Sep. 13, 1989, Pat. No. 4,941,364.

[30] Foreign Application Priority Data

Sep. 9, 1987 [GB] United Kingdom ................. 8721185
May 5, 1989 [GB] United Kingdom ................. 8910406

[51] Int. Cl.[5] ................................................ G01N 1/12
[52] U.S. Cl. ............................. 73/864.53; 73/DIG. 9
[58] Field of Search ......................... 73/864.51-864.59, 73/DIG. 9; 266/99

[56] References Cited

U.S. PATENT DOCUMENTS 3,452,602 7/1969 Hackett .......................... 73/DIG. 9
3,877,309 4/1975 Hanle ............................. 73/DIG. 9
4,067,242 1/1978 Judge ............................. 73/DIG. 9
4,211,117 7/1980 Cure .............................. 73/DIG. 9
4,941,364 7/1990 Haughton ....................... 73/DIG. 9

FOREIGN PATENT DOCUMENTS 1526144 4/1968 France ............................. 73/864.55

*Primary Examiner*—Robert Raevis
*Attorney, Agent, or Firm*—Shoemaker and Mattare, Ltd.

[57] ABSTRACT

A holder for a molten metal sampling device includes a pipe having a guidance chamber in a lower portion and a molten metal sampling device in an upper portion. The pipe is open downwardly and a closure element closes the opening. The closure element has a density such as to cause it to float upwardly in the molten metal being samples. A protective cover, preferably of two parts, encloses the closure element and a lower portion of the pipe. A retaining device such as a spring clip holds the separate parts of the protective cover together around the closure element and the lower part of the pipe. The retaining device is adapted to fail upon contact with the molten metal, thus releasing the portions of the protective cover so that they will separate and float upwards, whereupon the closure element also separates and floats away, allowing molten metal into the guidance chamber and the sampling device. The pipe and the closure element are both cylindrical and coaxial, and have substantially the same diameter. The closure element further has an outwardly projecting circumferential ledge remote from the pipe. The protective cover includes two similar halves constituting the parts, each half having a semicylindrical side wall of which one end lies juxtaposed against the ledge.

10 Claims, 3 Drawing Sheets

14
10
22
12
20
16
18
26
40
24
46
42
42
4
4
44
44

10
12
46
40
46
42

14
10
22
12
20
16
18
26
40
24
46
42
42
4
4
44
44

10
12
34
34
36
36
28
32
30
24a 46
48

42
42
40

44

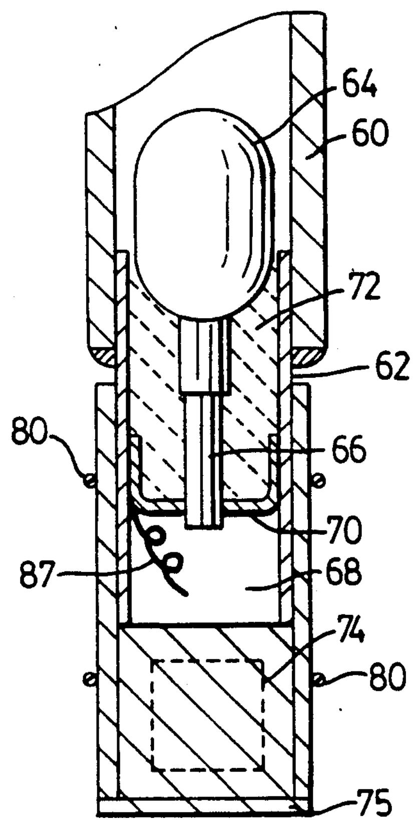
FIG. 6
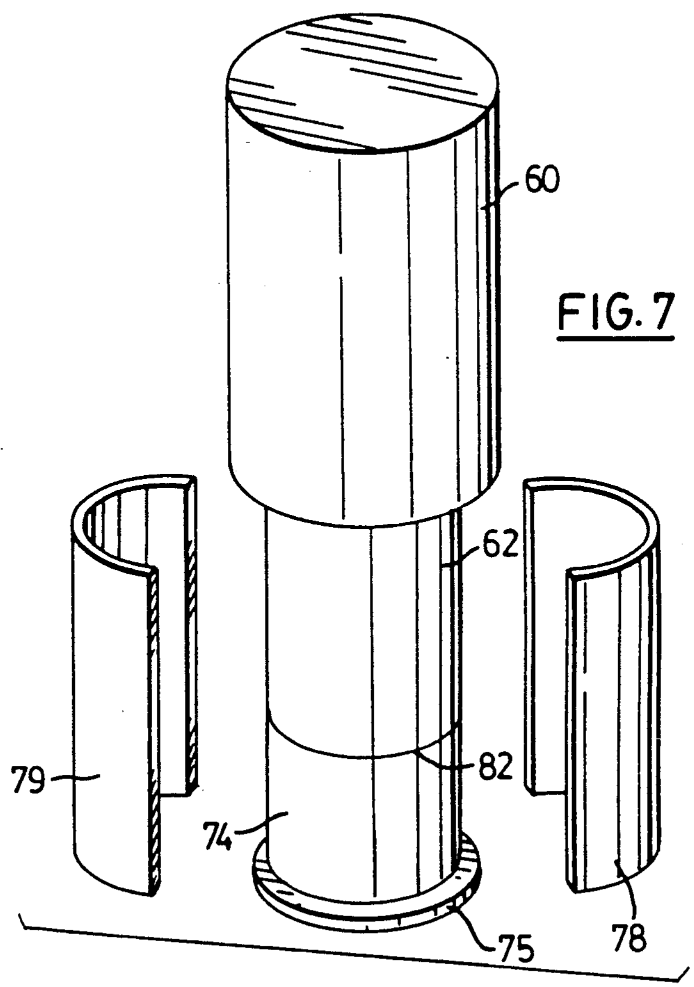
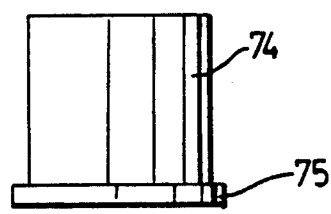
FIG. 8
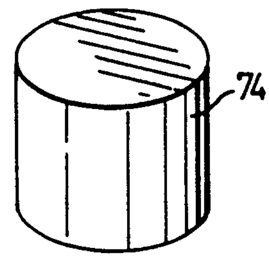
FIG. 9

60
62
74
75
90
92
92
94
96
96
98
98

60
100
92
100
75
90

HOLDER FOR MOLTEN METAL SAMPLING DEVICE

This is a continuation-in-part of U.S. Pat. application Ser. No. 240,506, filed Sept. 6, 1988, now Pat. No. 4,932,271; and of U.S. Pat. application Ser. No. 406,529, filed Sept. 13, 1989, now U.S. Pat. No. 4,941,364.

The present invention relates to molten metal sampling devices, especially to such devices with a non-diluting and non-contaminating protection cap and entrance system.

BACKGROUND OF THIS INVENTION

Prior samplers have been designed with a capping and entrance system that melted along with and into the molten material being sampled. This caused a source of undesirable contaminants to flow into the actual sample chamber. The prior method also allowed elements contained in the capping system to cause a diluting effect on similar elements contained in the molten batch material.

The location being sampled may contain extremely low (typically, 2 to 50 ppm) values of certain elements, for example, C, S, Mn, $O_2$, H and N, that must be accurately analyzed in order to produce a high quality product. At these minute ranges, any outside contamination or dilution can cause a significant error in accurate analysis.

Patents representative of the prior art in this area are as follows:

U.S. Pat. No. 4,428,245, issued Jan. 31, 1984 to Nakamura et al;
U.S. Pat. No. 4,007,641, issued Feb. 15, 1977 to Kelsey;
U.S. Pat. No. 4,557,152, issued Dec. 10, 1985 to Plessers et al;
U.S. Pat. No. 4,646,578 issued Mar. 3, 1987 to Lawrenz et al;
U.S. Pat. No. 4,170,139, issued Oct. 9, 1979 to Narita et al;
U.S. Pat. No. 4,250,753 issued Feb. 17, 1981 to Collins;
U.S. Pat. No. 4,140,019 issued Feb. 20, 1979 to Falk;
U.S. Pat. No. 4,112,772, issued Sept. 12, 1978 to McDevitt;
U.S. Pat. No. 4,037,478, issued July 26, 1977 to Cure;
U.S. Pat. No. 4,002,073, issued Jan. 11, 1977 to Collins;
U.S. Pat. No. 3,332,288, issued July 24, 1967 to Mladenovich;
U.S. Pat. No. 3,693,449, issued Sept. 26, 1972 to Collins;
U.S. Pat. No. 4,051,732 issued Oct. 5, 1979 to Falk;
U.S. Pat. No. 3,859,857, issued Jan. 14, 1975 to Falk;

In my U.S. Pat. application Ser. No. 240,506, entitled "Molten Metal Sampling Device", there is proposed a novel capping and entrance system that very much reduces contamination or dilution of the obtained sample. A cap is provided, which is rapidly released from the sampling device upon immersion in the molten metal, and simply floats away.

However, even with the improvement provided by my earlier invention, there remains a slight risk that small portions from the slag layer can be carried down to the region of the sampling device as the latter is plunged downwardly through the slag.

Accordingly, an object of one aspect of this invention is to further decrease the risk of contamination or dilution of an obtained sample.

In a general way, this object is achieved by providing an additional protective cover around the outside of the sampler, the additional protective cover being of a material which tends to repel slag components. The additional protective cover is a composite unit held together by a suitable clip or wire means, whereby the clip or wire fails upon contact with the molten metal, allowing the components of the additional protective cover to separate and float upwardly. While it may still occur that portions of the slag layer adhere to the outside of the additional protective cover, these same contaminants are carried away from the point of sampling along with the components of the additional protective cover as the latter float upwardly to the surface of the melt.

More particularly, this invention provides a holder for a molten metal sampling device, comprising:

a pipe which is elongated in a given direction, the pipe having an upper portion and a lower portion, the lower portion defining an internal guidance chamber and having an opening lying in a plane making an angle with respect to said given direction, the opening communicating with the guidance chamber, the upper portion being adapted to receive and retain the molten metal sampling device in such a way that molten metal in the guidance chamber can be sampled by the sampling device, a closure element for said opening, the closure element having a density such that it will seek to float upwardly in the molten metal being sampled, and a protective cover enclosing a portion of said closure element and a lower part of said pipe, the protective cover having at least two separate parts, and retaining means for holding the separate parts of the protective cover together around the closure element and the lower part of the pipe, the retaining means being adapted to fail upon contact with the molten metal, said pipe and said closure element both being cylindrical and coaxial, and having substantially the same diameters, the closure element further having an outwardly projecting circumferential ledge remote from the pipe, the protective cover comprising two similar halves constituting containing said parts, each half having a semi-cylindrical side wall of which one end lies in juxtaposition against said ledge.

GENERAL DESCRIPTION OF THE DRAWINGS

Two embodiments of this invention are illustrated in the accompanying drawings, in which like numerals denote like parts throughout the several views, and in which:

FIG. 1 is an elevational view of a sampler apparatus forming the focus of my co-pending U.S. Pat. application Ser. No. 406,529, filed on Sept. 13, 1989;

FIG. 6 is an axial sectional view through a sampler apparatus constructed in accordance with this invention;

FIG. 7 is an exploded perspective view of the apparatus shown in FIG. 6;

FIG. 8 is an elevational view of one of the components of the apparatus seen in FIG. 6;

FIG. 9 is an exploded view showing a possible construction for the element illustrated in FIG. 8;

DETAILED DESCRIPTION OF THE DRAWINGS

Figure 1:
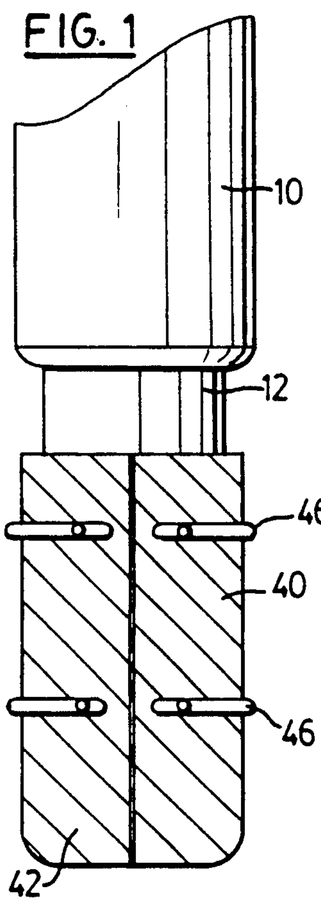
Figure 2:
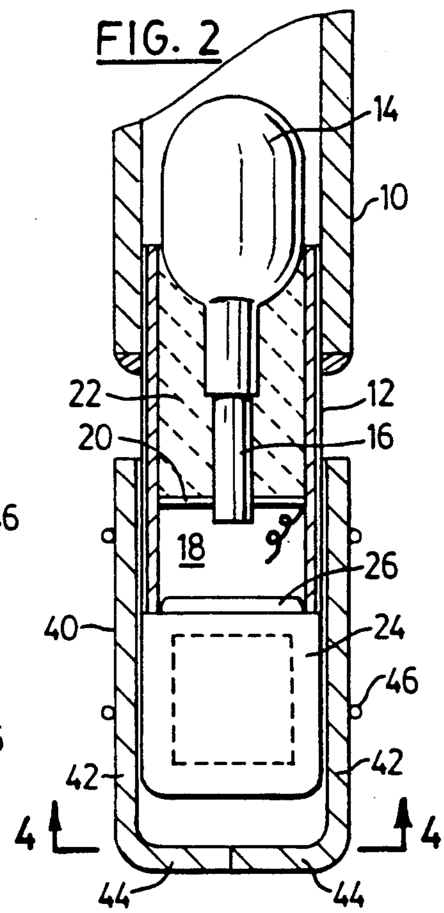
FIG. 2 is an axial sectional view through the apparatus of FIG. 1.
Figure 3:
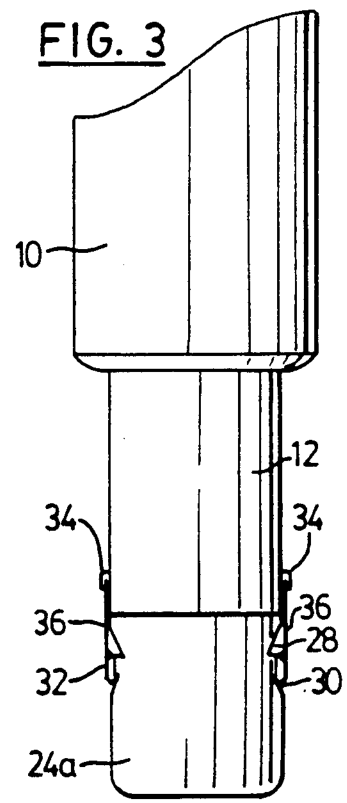
FIG. 3 is an elevational view of the apparatus of FIG. 1 with the outside protective cover removed.

Attention is first directed to FIGS. 1, 2 and 3, which show an external cardboard cylinder 10 with an open bottom end into which partly projects an internal pipe 12 which may be made of alumino silicate reinforced with fiberglass tape or other suitable material. Alternatively, the pipe 12 may be made of Mullite ($3Al_2O_3.2SiO_2$) coated with a Boron Nitride Lubricoat, to discourage liquid slag from adhering to the tube. The pipe 12 is square-cut at both ends. Within the upper end is lodged a "lollipop"-shaped sampler 14 of known construction which communicates with a tube 16 which is open at the bottom to allow molten metal to enter the sampler 14 after it has entered a chamber 18 lying within the pipe 12 but below a partition 20. Between the partition 20 and the upper end of the internal pipe 12 is provided refractory material 22 or the equivalent, which has the effect of securing the sampler 14 in place. The open bottom end of the pipe 12 is closed by a cap 24 which may be of alumino silicate reinforced with fiberglass tape. Alternatively, the cap 24 may be made of Mullite ($3Al_2O_3.2SiO_2$) coated with Boron Nitride. This item may be either solid or hollow (the hollowness is shown by the broken lines in FIG. 2), and includes an upward protuberance 26 which registers within the open bottom end of the inner pipe 12.

FIG. 3 shows a slightly different configuration for the cap, indicated at 24*a*. The cap 24*a* includes two surrounding grooves at 28 and 30, which between them define an outwardly projecting flange 32. Small eyelets 34 at opposite sides of the inner pipe 12 (FIG. 3) each secure one end of a wire 36 which engages a suitable opening in the flange 32. Shortly after the cap 24*a* contacts the molten metal, the wires 36 fail by melting, allowing the cap 24*a* to float freely away, thus allowing molten metal into the chamber 18 (FIG. 2). It is to be understood that the cap 24 in FIG. 2 would be secured by some analogous method to that described with respect to FIG. 3.

As an alternative to the use of wires 36 shown in FIG. 3, it is possible to employ fiberglass tape approximately one inch wide to join and seal the parts together. It has been found that the use of tape is less expensive than the use of wires, and functions quite satisfactorily. As a further alternative, a magnetic fastening system could also be used.

Figure 5:
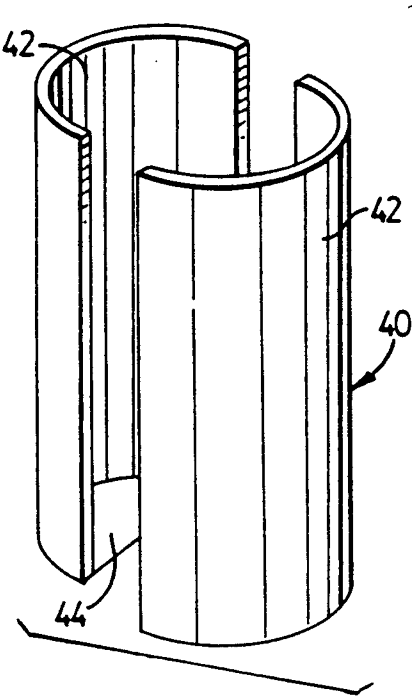
FIG. 5 is a perspective view of one of the components shown in FIG. 2.

In FIG. 1 there is shown an outer protective cover 40 which is seen in FIG. 5 to include two semi-cylindrical side wall portions 42, each with a semi-circular bottom wall 44 (only one visible in FIG. 5). The two-part protective cover 40 is adapted snugly to surround the cap 24 and a lower portion of the inner pipe 12. The two portions of the outer protective cover 40 are shown to be held in place (in the embodiment illustrated) by two spring clips 46.

Figure 4:
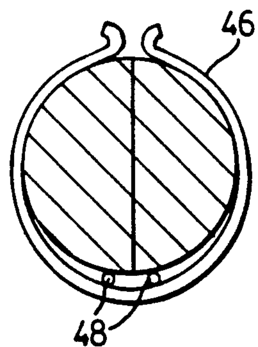
FIG. 4 is a cross-sectional view taken at the line 4—4 in FIG. 2.

Preferably, as shown in FIG. 4, each clip 46 is held in spaced relation away from the outer surface of the protective cover 40 by a pair of protuberances 48. This allows the melt to fully surround at least a portion of each spring clip 46, thus melting the clip more readily upon entry into the melt, whereby the two halves of the outer protective cover 40 spread apart and drift up to the surface of the melt.

It has been found that the provision of the outer protective cover 40 virtually eliminates the risk that slag components will remain close to the bottom of the pipe 12 during the taking of the sample.

The two-part outer protective cover 40 may be made of alumino silicate reinforced with fiberglass tape. Alternatively, these parts may be made of Mullite coated with Boron Nitride. On the basis of trials for testing purposes, it is believed that the alumina silicate tends to repel contaminants and to discourage the sticking of slag components to its outer surface.

Attention is now directed to FIGS. 6–9, for a description of the present invention.

As with the previously described apparatus, the apparatus shown in FIG. 6 includes an external cardboard cylinder 60 with an open bottom end into which partly projects an internal pipe 62 which may be made either of alumino silicate reinforced with fiberglass tape, Mullite coated with a Boron Nitride Lubricoat, or any equivalent material. The pipe 62 is square-cut at both ends. Within the upper end is lodged a "lollipop"-shaped sampler 64 essentially the same as the sampler 14 shown in FIG. 2. The sampler 64 communicates with a tube 66 which is open at the bottom to allow molten metal to enter the sampler 64 after it has entered a chamber 68 lying within the pipe 62 but below a partition element 70. Between the partition element 70 and the upper end of the internal pipe 62 is provided refractory material 72 or the equivalent, which secures the sampler 64 in place. The open bottom end of the pipe 62 is closed by a cap 74 which may be made of alumino silicate reinforced with fiberglass tape. Alternatively, the cap 74 may be made of Mullite coated with Boron Nitride. The cap 74 may be either solid or hollow.

FIGS. 6 to 9 show the cap 74 to be essentially a right circular cylinder having an outwardly projecting circumferential ledge 75. The cap 74 is intended to be retained in place against the bottom end of the pipe 62 by the same means already described with reference to FIG. 3 (but not illustrated in FIGS. 6–9). Alternatively, and as mentioned earlier in connection with FIGS. 1–5, it would be possible to employ fiberglass tape approximately one inch wide to join and seal the pipe 62 and the cap 74.

The present invention further incorporates a protective cover comprising two similar halves 78 and 79, each half consisting of a semi-cylindrical side wall configured in such a way that, when fitted against the pipe 62 and the cap 74, the lower edges of the halves 78 and 79 can lie in juxtaposition against the ledge 75. this is clearly illustrated in FIG. 6.

As seen in FIG. 6, the halves 78 and 79 can be secured in place by circumferential C-clips 80, or any other suitable provision. It is to be understood that, upon plunging the apparatus downwardly into the melt, the clips 80 would melt and allow the halves 78 and 79 to separate and float upwardly to the top of the melt.

In the event that slag components adhere to the outside of the halves 78 and 79 during passage through the slag layer, such adhering material will be carried upwardly and away from the junction 82 between the caps 74 and the pipe 62. Thus, when the junction 82 opens, due to the fact that the cap 74 is released and floats upwardly, no slag or slag components will contaminate the molten metal entering the chamber 68 (see FIG. 6) within the bottom of the pipe 62.

In a manner similar to that shown in FIG. 4, the C-clips 80 of FIG. 6 may, at one portion of the periphery, be held in spaced relation away from the outer surface of the halves 78 and 79, thus allowing the molten metal to melt the clips 80 more readily upon entry into the melt. This spacing-away of the C-clips 80 has not been illustrated, in order to avoid needless duplication.

FIG. 9 shows one way in which the cap 74 can be manufactured. In FIG. 9, a disc 85 is glued or otherwise adhered to the bottom of a right circular cylinder 74, with the disc 85 effectively providing the ledge 75 at its outer periphery.

In FIG. 6, the chamber 68 is seen to enclose a thin deoridant wire 87, for the purpose of "killing" the entering molten steel by removing oxygen therefrom. The wire 87 would typically be of aluminum, titanium or zirconium. Those skilled in this art will be fully familiar with such provision.

Figure 11:
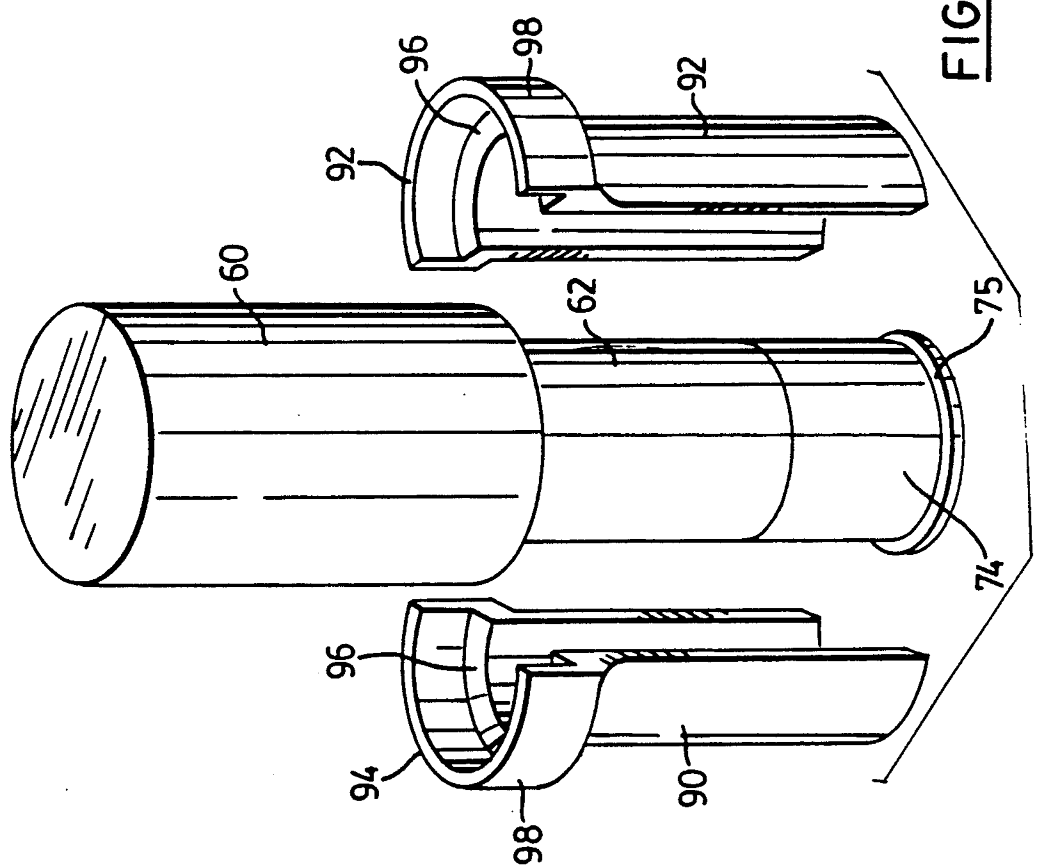
FIG. 11 is an exploded perspective view of the apparatus shown in FIG. 10.
Figure 10:
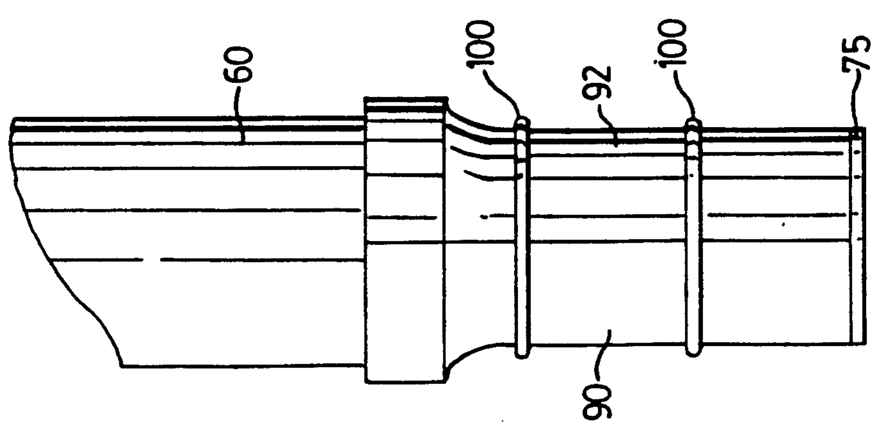
FIG. 10 is an elevational view of a further embodiment of the sampler apparatus constructed in accordance with this invention.

Attention is now directed to FIGS. 10 and 11, showing a further embodiment. As seen in FIG. 11, the external cardboard cylinder 60, the internal pipe 62, the cap 74 and all of the internal portions within these members, remain the same as those shown in FIG. 7 (and have the same numerals). The cap 74 has the outwardly projecting circumferential ledge 75, again as pictured in FIG. 7.

In the embodiment shown in FIGS. 10 and 11, the protective cover comprises two similar halves 90 and 92, each half consisting of a semi-cylindrical side wall portion in the lower part, with an integral expanded portion 94 at the top, adapted to receive snugly the lower end of the external cardboard cylinder 60. As is particularly illustrated in FIG. 11, each of the halves 90 and 92 incorporates an internal, outwardly projecting step 96 and an upstanding ring portion 98 at the outer edge of the step 96. The outer wall of the lower cylindrical portion, in each case, curves smoothly outwardly and upwardly to meet the bottom of the outer surface of the ring portion 98.

FIG. 10 is a view similar to that of FIG. 1, but corresponding to FIG. 11. In FIG. 10, two C-clips 100 are provided to hold the halves 90 and 92 in place until the sampling device has been immersed in the melt. At that point the C-clips 100 melt, allowing the halves 90 and 92 to float upwardly and away from the remainder of the structure. The cap 74 is then released in the same manner as described earlier in connection with the other figures, allowing a sample to be taken. It will be appreciated that the provision of the upper portion of the halves 90 and 92 allows a greater degree of isolation at the sample-taking location, thus further ensuring that no contamination will take place.

While one embodiment of this invention has been illustrated in the accompanying drawings and described hereinabove, it will be evident to those skilled in the art that changes and modifications may be made therein without departing from the essence of this invention, as set forth in the appended claims.

The Embodiments of the invention in which an Exclusive Property or Privilege is claimed are defined as follows:

1. A holder for a molten metal sample device, comprising:

a pipe which is elongated in a given direction, the pipe having an upper portion and a lower portion, the lower portion defining an internal guidance chamber and having an opening lying in a plane making an angle with respect to said given direction, the opening communicating with the guidance chamber, the upper portion being adapted to receive and retain the molten metal sampling device in such a way that molten metal in the guidance chamber can be sampled by the sampling device, a closure element for said opening, the closure element having a density such that it will seek to float upwardly in the molten metal being sampled, and a protective cover enclosing a portion of said closure element and a lower part of said pipe, the protective cover having at least two separate parts, and retaining means for holding the separate parts of the protective cover together around the closure element and the lower part of the pipe, the retaining means being adapted to fail upon contact with the molten metal, said pipe and said closure element both being cylindrical and coaxial, and having substantially the same diameters, the closure element further having an outwardly projecting circumferential ledge remote from the pipe, the protective cover comprising two similar halves constituting said parts, each half having a semi-cylindrical side wall of which one end lines in juxtaposition against said ledge.

2. The holder claimed in claim 1, in which said retaining means is constituted by a metallic element at least partly surrounding the protective cover, the metallic element having at least one location where it is held spaced away from the protective cover, whereby the metallic element will fail by melting at said at least one location.

3. The holder claimed in claim 2, in which the closure element is held against said opening by a further retaining means which is adapted to fail upon contact with the molten metal.

4. The holder claimed in claim 3, in which said further retaining means is a further metallic element, said further metallic element having at least one location where it is held spaced away from the closure element, whereby said further metallic element will fail by melting at said at least one location.

5. The holder claimed in claim 4, in which said plane is substantially perpendicular to the common axis of the pipe and the closure element.

6. The holder claimed in claim 1, in which said pipe is received within an external hollow cylindrical member, and in which each half of the protective cover has an enlarged portion at the top which snugly surrounds the lower portion of the cylindrical member, thus fully covering the portion of the pipe not received within the cylindrical member.

7. The holder claimed in claim 6, in which said retaining means is constituted by a metallic element at least partly surrounding the protective cover, the metallic element having at least one location where it is held spaced away from the protective cover, whereby the metallic element will fail by melting at said at least one location.

8. The holder claimed in claim 7, in which the closure element is held against said opening by a further retaining means which is adapted to fail upon contact with the molten metal.

9. The holder claimed in claim 8, in which said further retaining means is a further metallic element, said further metallic element having at least one location where it is held spaced away from the closure element, whereby said further metallic element will fail by melting at said at least one location.

10. The holder claimed in claim 9, in which said plane is substantially perpendicular to the common axis of the pipe and the closure element.

* * * * *